(12) United States Patent
Zhou et al.

(10) Patent No.: US 10,017,530 B2
(45) Date of Patent: Jul. 10, 2018

(54) FLUORINATION METHOD FOR PHOSPHONITRILIC CHLORIDE TRIMER AND ITS DERIVATIVES

(71) Applicant: Shandong Zeshi New Materials Technology Co., Ltd., ZiBo (CN)

(72) Inventors: Xiao Zhou, ZiBo (CN); QingChang Lu, ZiBo (CN)

(73) Assignee: Shandong Zeshi New Materials Technology Co., Ltd., Zibo (CN)

( * ) Notice: Subject to any disclaimer, the term of this patent is extended or adjusted under 35 U.S.C. 154(b) by 0 days.

(21) Appl. No.: 15/566,721

(22) PCT Filed: Oct. 29, 2015

(86) PCT No.: PCT/CN2015/093219
§ 371 (c)(1),
(2) Date: Oct. 15, 2017

(87) PCT Pub. No.: WO2016/165310
PCT Pub. Date: Oct. 20, 2016

(65) Prior Publication Data
US 2018/0118768 A1    May 3, 2018

(30) Foreign Application Priority Data

Apr. 14, 2015 (CN) .......................... 2015 1 0175894

(51) Int. Cl.
C07F 9/659 (2006.01)
C07F 9/6593 (2006.01)
C07F 9/6581 (2006.01)

(52) U.S. Cl.
CPC .......... *C07F 9/659* (2013.01); *C07F 9/65812* (2013.01); *C07F 9/65815* (2013.01)

(58) Field of Classification Search
None
See application file for complete search history.

(56) References Cited

U.S. PATENT DOCUMENTS

2014/0178752 A1   6/2014  Park et al.

FOREIGN PATENT DOCUMENTS

| CN | 101407527 A | 4/2009 |
| CN | 102702268 A | 10/2012 |
| CN | 104788495 A | 7/2015 |

OTHER PUBLICATIONS

Elias ("Chemistry of diphenyltetrafluorophosphazene: Reactions with lithiated diols" Journal of Fluorine Chemistry, 127, 2006, p. 1046-1053).*
Sheng Han et al., "Application of Ionic Liquids in Organic Fluorination Reaction", Chemical Reagents, vol. 34, No. 1, Jan. 31, 2012 (Jan. 31, 2012), pp. 35-40, see the whole document, particularly p. 37, point 3 the part of "nucleophilic fluorination".
Qiong Wang, "Catalytic Synthesis of Phosphazene Compounds in Ionic Liquids", Chinese Master's Theses Full-test Database Engineering Science and Technology I, No. 7 vol. 2014.

* cited by examiner

*Primary Examiner* — Jafar Parsa
*Assistant Examiner* — Amy C Bonaparte
(74) *Attorney, Agent, or Firm* — Gokalp Bayramoglu

(57) ABSTRACT

The present invention relates to a fluorination method for phosphonitrilic chloride trimer and its derivatives including using phosphonitrilicchloride or partially substituted phosphonitrilic chloride trimer as raw material to fluorinate with fluorinating agent in an ionic liquid to replace the chlorine in chloro-cyclotriphosphazene molecule. The present invention uses non-volatile and pollution free ionic liquids as solvent, and just controls a distillation temperature to get a hexafluorocyclotriphosphazene or derivatives thereof with high-purity. It overcomes the shortcoming of the average solvent system that the solvent forms azeotrope with products. The post-process is simple. The production rate is high, and the ionic liquid can be recycled. The present invention produces products with high purity.

7 Claims, No Drawings

FLUORINATION METHOD FOR PHOSPHONITRILIC CHLORIDE TRIMER AND ITS DERIVATIVES

CROSS REFERENCE TO RELATED APPLICATIONS

This application is the national phase entry of International Application No. PCT/CN2015/093219, filed on Oct. 29, 2015, which is based upon and claims priority to Chinese Patent Application No. CN2015101758942, filed on Apr. 14, 2015, the entire contents of which are incorporated herein by reference.

TECHNICAL FIELD

This invention relates to a fluorination method for phosphonitrilic chloride trimer and its derivatives.

BACKGROUND

Phosphazenes have both the good flame retardant property of phosphorus flame retardant and flame retardant synergism of nitrogen compound. Without the need to add any other assisting flame retardants, they have advantages like good flame retardant efficiency, good thermal stability, no toxicity, less smoke and self-extinguishment and are therefore generally recognized as one of the future development directions of fire retardant. Various kinds of phosphazene flame retardants are synthesized and used in flame retardant research of various materials. At the same time, phosphazenes can also be used in preparation of high temperature resistant, low temperature resistant and oxidation resisting special rubber and elastic materials used in military and aerospace industries. Chloro-cyclotriphosphazene has good flame retardant efficiency. However, it has easy hydrolysis and chlorine is highly corrosive to battery system. Recently, it is found in research that replacing chlorine with fluorine can get a functional phosphazene derivative with hydrolysis resistance, lower viscosity and better compatibility. Fluoro-phosphazenes can also be used as an efficient flame retardant for lithium ion battery. Currently, phosphazenes are usually fluoridized in organic small molecule solvent and then make distillation and fractionation to the fluoride generated. As the organic small molecule is volatile and forms azeotrope with fluoro-cyclotriphosphazene, which makes purification difficult. It wastes solvents and increases cost.

SUMMARY

To solve the above problem, this invention provides an efficient and non-volatile fluorination system in which ionic liquid is used as reactive system solvent to improve fluorination efficiency of cyclotriphosphazene and its derivatives and reduce purification cost.

The technical plan adopted in this invention is as follows:

A fluorination method for phosphonitrilic chloride trimer and its derivatives, characterized in that (including the following steps):

Dissolve phosphonitrilic chloride trimer or its derivatives in ionic liquid, add fluorinating agent and control the temperature to have fluorination. Then distill to prepare high-purity hexafluorocyclotriphosphazene or its derivatives.

The chemical formula of the described phosphonitrilic chloride trimer and its derivatives is:

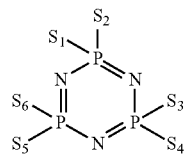

Wherein: There is at least one chlorine in $S_1$-$S_6$, and $S_1$-$S_6$ come independently from alkyl, alkoxy, fluoroalkoxy, aryl, carboxyl, hydroxy, cyanogroup, nitro, ether oxygen group and halogen.

The chemical formula of the described ionic liquid is:

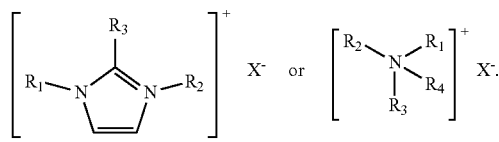

Substitution in the above chemical formula is mono, binary or triple substitution, and moreover, R1, R2 and R3 are independently selected from alkyl (when the carbon atom is 0, R, R2 or R3 is hydrogen), alkoxy, aryl, carboxyl, hydroxy, cyanogroup, nitro, ether oxygen group and halogen of carbon atom in 0-20.

The optimal and substitution groups R 1, R2 and R3 are independently selected from the following groups: methyl, ethyl, propyl, butyl, vinyl, allyl, butenyl, vinylidene, phenyl or benzyl.

Wherein, the anion X is at least one from the following: F—, PF6-, BF4-, TFSI—, FSI—, BOB— and ClO4-.

The fluorinating agent described is one or multiple combinations of ammonium, lithium, sodium, potassium, rubidium, calcium, magnesium, aluminum, chromium, iron, cobalt, antimony, nickel, copper, zinc, titanium or rare earth fluorides, and the optimal fluorides are sodium fluoride and potassium fluoride.

Temperature of the described fluorination is 10-300° C., and the optimal temperature is 100-130° C. Time for the described reaction is 2-98 hours, and the optimal time is 12-15 hours. Temperature of the distillation described is 40-300° C. The optimal temperature is 10° C. higher than the boiling point of the product.

Compared with current technology, this invention uses non-volatile and pollution free ionic liquid, and just controls distillation temperature to get high-purity hexafluorocyclotriphosphazene or its derivatives. It overcomes the shortcoming that solvent of average solvent system forms azeotrope with product. The post-process is simple, product purity and production rate are high, and the ionic liquid can be used repeatedly.

DETAILED DESCRIPTION OF THE INVENTION

Embodiment 1

Take 0.1 mole phosphonitrilic chloride trimer and add it into a flask with 100 ml 1-benzyl-3-methylpyridinium hexafluorophosphate ionic liquid and then add 1 mole sodium fluoride. Fluoridate 10 hours at 130° C. and then distill at 60° C. to get high-purity hexafluorocyclotriphosphazene.

Embodiment 2

Take 0.1 mole ethoxy pentachloride cyclotriphosphazene and add it into a flask with 100 ml 1-allyl-3-methylimidazolium tetrafluoroborate ionic liquid and then add 1 mole sodium fluoride. Fluoridate 12 hours at 130° C. and then distill at 160° C. to get high-purity pentafluoro ethoxy cyclotriphosphazene.

Embodiment 3

Take 0.1 mole pentachloride trifluoro ethoxy cyclotriphosphazene and add it into a flask with flux unit and containing 100 ml 1-phenyl-3-methylimidazolium tetrafluoroborate ionic liquid and then add 1 mole potassium fluoride and 0.5 mole sodium fluoride. Fluoridate 20 hours at 200° C. and then distill at 180° C. to get high-purity pentafluoro ethoxy cyclotriphosphazene.

Embodiment 4

Take 0.1 mole dichloro tetrabutoxy cyclotriphosphazene and add it into a flask with flux unit and containing 100 ml 1-methyl-3-methylimidazolium tetrafluoroborate ionic liquid and then add 0.5 mole potassium fluoride and 0.5 mole calcium fluoride. Fluoridate 16 hours at 280° C. and then distill at 220° C. to get high-purity difluoro tetrabutoxy cyclotriphosphazene.

Embodiment 5

Take 0.1 mole pentachloride phenoxy cyclotriphosphazene and add it into a flask with flux unit and containing 100 ml 1-ethylene-3-methylimidazolium tetrafluoroborate ionic liquid and then add 0.8 mole potassium fluoride. Fluoridate 16 hours at 50° C. and then distill at 240° C. to get high-purity pentafluoro phenoxy cyclotriphosphazene.

Embodiment 6

Take 0.1 mole pentachloride phenoxy cyclotriphosphazene and add it into a flask with 50 ml 1-phenoxy-3-methylimidazolium tetrafluoroborate and 50 ml 1-allyl-3-imethylimidazolium hexafluorophosphate ionic liquid and then add 0.8 mole potassium fluoride and 0.2 mole zinc fluoride. Fluoridate 16 hours at 50° C. and then distill at 240° C. to get high-purity pentafluoro phenoxy cyclotriphosphazene.

What is claimed is:

1. A fluorination method for phosphonitrilic chloride trimer and derivatives thereof, comprising the following steps:
    dissolving a phosphonitrilic chloride trimer or derivatives thereof into an ionic liquid, adding a fluorinating agent to obtain a solution, and maintaining the solution in a temperature for fluorination; and,
    distilling the solution after fluorination at atmospheric pressure to get a hexafluorocyclotriphosphazene or derivatives thereof;
    wherein a chemical formula of the phosphonitrilic chloride trimer and derivatives thereof is:

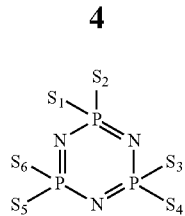

wherein each one of $S_1$-$S_6$ is selected from the group consisting of alkyl, alkoxy, fluoroalkoxy, aryl, carboxyl, hydroxy, cyano, nitro, ether, and halogen; and wherein at least one of $S_1$-$S_6$ is chlorine.

2. The fluorination method for phosphonitrilic chloride trimer and derivatives thereof according to claim 1, wherein a chemical formula of the ionic liquid is:

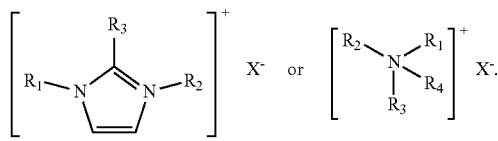

wherein each of R1, R2, R3, and R4 is selected from the group consisting of alkyl, alkoxy, aryl, carboxyl, hydroxy, cyano, nitro, ether, hydrogen, and halogen, wherein each of R1, R2, R3, and R4 have 0-20 carbon atoms; wherein at least one of the R1, R2, or R3 is not hydrogen; and
wherein the anion X is one or more selected from the group consisting of $F^-$, $PF_6^-$, $BF_4^-$, $TFSI^-$, $FSI^-$, $BOB^-$ $ClO_4^-$.

3. The fluorination method for phosphonitrilic chloride trimer and derivatives thereof according to claim 2, wherein each of R1, R2 and R3 is selected from the group consisting of methyl, ethyl, propyl, butyl, phenyl, and benzyl.

4. The fluorination method for phosphonitrilic chloride trimer and derivatives thereof according to claim 1, wherein the fluorinating agent is one or more selected from the group consisting of ammonium fluoride, lithium fluoride, sodium fluoride, potassium fluoride, rubidium fluoride, calcium fluoride, magnesium fluoride, aluminum fluoride, chromium fluoride, iron fluoride, cobalt fluoride, antimony fluoride, nickel fluoride, copper fluoride, zinc fluoride, titanium fluoride and rare earth fluorides.

5. The fluorination method for phosphonitrilic chloride trimer and derivatives thereof according to claim 4, wherein the fluorinating agent is sodium fluoride and/or potassium fluoride.

6. The fluorination method for phosphonitrilic chloride trimer and derivatives thereof according to claim 1, wherein the temperature for fluorination is 10-300° C., the fluorination is carried out for 2-98 hours and a temperature for distillation is 40-300° C.

7. The fluorination method for phosphonitrilic chloride trimer and derivatives thereof according to claim 1, wherein the temperature for fluorination is 0° C.-130° C., the fluorination is carried for a time duration of 12-15 hours and the temperature for distillation is 10° C. higher than the boiling point of the product.

* * * * *